United States Patent
Frassetto et al.

(10) Patent No.: US 12,410,119 B2
(45) Date of Patent: Sep. 9, 2025

(54) PROCESS FOR THE PREPARATION OF A-METHYL-[4-(NITRO)-2-(TRIFLUOROMETHYL)-BENZYL NITRATE

(71) Applicant: BASF AGRO B.V., Arnhem (NL)

(72) Inventors: Timo Frassetto, Ludwigshafen (DE); Florian Vogt, Ludwigshafen (DE); Swapnil Yerande, Pune (IN); Christiane Alznauer, Ludwigshafen (DE); Sebastian Illies, Ludwigshafen (DE); Philip Muelheims, Ludwigshafen (DE); Daniel Saelinger, Ludwigshafen (DE); Robin Thiele, Ludwigshafen (DE); Heinz Friedrich Sutoris, Ludwigshafen (DE)

(73) Assignee: BASF AGRO B.V., Arnhem (NL)

( * ) Notice: Subject to any disclaimer, the term of this patent is extended or adjusted under 35 U.S.C. 154(b) by 884 days.

(21) Appl. No.: 17/634,276

(22) PCT Filed: Sep. 2, 2020

(86) PCT No.: PCT/EP2020/074478
§ 371 (c)(1),
(2) Date: Feb. 10, 2022

(87) PCT Pub. No.: WO2021/047978
PCT Pub. Date: Mar. 18, 2021

(65) Prior Publication Data
US 2022/0324790 A1 Oct. 13, 2022

(30) Foreign Application Priority Data

Sep. 12, 2019 (EP) .................... 19196848

(51) Int. Cl.
| | |
|---|---|
| *C07C 201/02* | (2006.01) |
| *C07C 201/08* | (2006.01) |
| *C07C 201/16* | (2006.01) |
| *C07C 203/02* | (2006.01) |
| *C07C 205/11* | (2006.01) |

(52) U.S. Cl.
CPC .......... *C07C 201/02* (2013.01); *C07C 201/08* (2013.01); *C07C 201/16* (2013.01); *C07C 203/02* (2013.01); *C07C 205/11* (2013.01)

(58) Field of Classification Search
CPC ... C07C 201/02; C07C 201/08; C07C 201/16; C07C 203/02; C07C 205/11

USPC ........................................................ 558/480
See application file for complete search history.

(56) References Cited

U.S. PATENT DOCUMENTS

| | | | |
|---|---|---|---|
| 4,846,875 A | 7/1989 | Chang | |
| 2011/0190302 A1 | 8/2011 | Greig et al. | |

FOREIGN PATENT DOCUMENTS

| | | |
|---|---|---|
| CN | 101589038 A | 11/2009 |
| CN | 106699729 A | 5/2017 |
| GB | 735545 A | 8/1955 |
| GB | 804467 A | 11/1958 |
| WO | WO-87/04049 A1 | 7/1987 |
| WO | WO-98/55437 A1 | 12/1998 |
| WO | WO-2000/69800 A2 | 11/2000 |
| WO | WO-2005/063720 A1 | 7/2005 |
| WO | WO-2006/034333 A2 | 3/2006 |
| WO | WO-2013/007767 A1 | 1/2013 |
| WO | WO-2014/082871 A1 | 6/2014 |

OTHER PUBLICATIONS

"Meditsinskaya Promyshlennost SSSR", vol. 10, Issue 4, 1956, pp. 9-10.
Kochergin, et al., "Synthesis of ketones, ketoaldehydes, and ketoacids from nitroesters" Pharmaceutical Chemistry Journal, vol. 28, Issue 4, Apr. 1994, pp. 271-273.
Teng, et al., "Synthesis and characterization of trifluoromethyl substituted styrene polymers and copolymers with methacrylates: Effects of trifluoromethyl substituent on styrene", Polymer, vol. 52, Issue 4, Feb. 17, 2011, pp. 949-953.
Yagupolskii, et al., "Synthesis Of Para-Nitrophenylhalomethyl Carbinols", Zhurnal Obshchei Khimii, vol. 28, Issue 6, 1958, pp. 1608-1610.
International Application No. PCT/EP2020/074478, International Search Report and Written Opinion, mailed Nov. 23, 2020.
International Application No. PCT/EP2020/074478, International Preliminary Report on Patentability, dated Mar. 15, 2022.
A.L. Shul'tsev, "Synthesis of aromatic ketones", Russian Journal of General Chemistry, vol. 83, Issue 4, May 23, 2013, pp. 773-774.
Sysolyatin, et al., "p-Tyrosol: a new synthetic method and new types of pharmacological activity", Russian Chemical Bulletin, vol. 64, Sep. 27, 2016, pp. 2210-2214.

*Primary Examiner* — Kahsay Habte

(57) ABSTRACT

The present invention relates to a process for the preparation of α-methyl-[4-(nitro)-2-(trifluoromethyl)]-benzyl nitrate and to the α-methyl-[4-(nitro)-2-(trifluoromethyl)]-benzyl nitrate.

15 Claims, No Drawings

PROCESS FOR THE PREPARATION OF A-METHYL-[4-(NITRO)-2-(TRIFLUOROMETHYL)-BENZYL NITRATE

CROSS-REFERENCE TO RELATED APPLICATIONS

This is the U.S. national phase of International Application No. PCT/EP2020/074478, filed Sep. 2, 2020, which claims the benefit of European Patent Application No. 19196848.6, filed on Sep. 12, 2019.

The present invention relates to a process for the preparation of α-methyl-[4-(nitro)-2-(trifluoromethyl)]-benzyl nitrate.

α-methyl-[4-(nitro)-2-(trifluoromethyl)]-benzyl nitrate (I) is a valuable substrate for synthesis of pesticidally active compounds. Therefore, there is a need for processes that easily make it available.

One of the ways for preparing nitro compounds is the nitration of the respective precursors.

GB 735545, Meditsinskaya Promyshlennost SSSR, 1956, 10 (4), pp. 9-10 and Zhurnal Obshchei Khimii, 1958, 28, 1608-10 describe the nitration of α-(alkyl or haloalkyl)-benzyl alcohols, wherein the phenyl ring is unsubstituted or substituted in o- or m-positions. The substrates are reacted with the nitric acid in the presence of the sulfuric or sulfanilic acid. Usually, mixtures of regioisomeric nitro-benzyl nitrates are formed. The yield of p-nitro-benzyl nitrates amounts to 40 to 70%.

CN106699729 and WO 2005/063720 describe the nitration of 2-trifluoromethyl-benzyl alcohol using the nitric acid in the presence of the sulfuric acid yielding 2-trifluoromethyl-4-nitro-benzyl alcohol (yield 42%) and 2-trifluoromethyl-4-nitro-benzyl nitrate respectively (yield 38%).

The yields are in general unsatisfactory, especially in view of an upscale to industrially relevant amounts. Additionally, some of these reactions require a large excess of the nitric acid. Further, it is well known that nitration reactions are usually highly exothermic and have high risk of runaway to explosion. The nitrated aromatic products must be handled carefully because of their explosive potential. For these reasons, safety issues must be always kept in mind when developing nitration processes.

Therefore, it was an object of the present invention to develop a process for the preparation of α-methyl-[4-(nitro)-2-(trifluoromethyl)]-benzyl nitrate, which method is safe, cheap and leads to the desired product in high yield, hence being suitable for an upscale to industrially relevant amounts.

It has now surprisingly been found a highly efficient process for nitration of α-methyl-2-(trifluoromethyl)-benzyl alcohol affording α-methyl-[4-(nitro)-2-(trifluoromethyl)]-benzyl nitrate in high yields.

Accordingly, the present invention relates to a process for the preparation of the compound of formula (I)

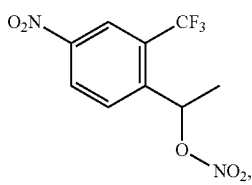

comprising the following step:
(i) reacting a compound of formula (II)

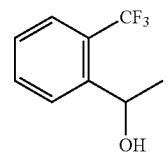

with the nitric acid in the presence of the sulfuric acid or oleum, wherein the nitric acid is used in an amount of 2 to 20 mole equivalents per 1 mole of the compound (II).

The compound of formula (I) is also part of the present invention.

In the step (i) compound (A) is formed as an intermediate compound. Compound (A) is also part of the present invention.

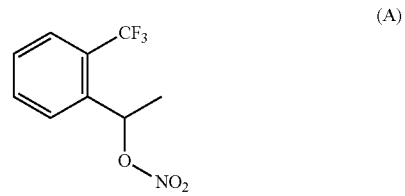

The process according to the present invention entails a series of advantages. It is safe, cheap and leads to the product in high yields. Undesired side reactions leading to unwanted by-products (like oxidation or elimination of the hydroxy-group or nitration in e.g. m- or o-positions) are minimized. The nitration occurs regioselective and nearly quantitative. The process can be carried out at a room temperature and does not require sophisticated cooling equipment. If desired, the product can be employed in the next reaction step without purification. According to some embodiments, the amount of nitric and/or sulfuric acid can be significantly reduced. Any of these advantages saves resources and energy and makes the process industrially simple and environmentally friendly.

Further embodiments of the invention are evident from the claims, the description and the examples. It is to be understood that the single features of the subject matter of the invention described herein can be applied not only in the combination given in each particular case but also in other combinations, without leaving the scope of the invention.

Starting compound (II) is commercially available or can be synthesized as known to the skilled person, e.g. from Polymer 52, (2011), 949-953.

The step (i) according to the present invention can be carried out batchwise or continuously. According to one embodiment, it is carried out batchwise. According to another embodiment, it is carried out continuously.

Nitric acid suitable for the present invention preferably has a concentration of at least 20 mol %. Usually it has a concentration of from 20 to 100 mol %, preferably from 60 to 100 mol %, more preferably from 80 to 100 mol %, most preferably from 90 to 100 mol %, particularly preferably from 95 to 100 mol %. It can contain dissolved nitrogen dioxide or be essentially free thereof. Essentially free means that it contains 0.5 mol % or less of dissolved nitrogen dioxide.

According to one specific embodiment, the nitric acid is a red fuming nitric acid.

According to another specific embodiment, the nitric acid is a white fuming nitric acid (also called 100% nitric acid).

According to another specific embodiment, the nitric acid is prepared in situ by contacting a nitrate salt, such as NaNO$_3$ or KNO$_3$ with the sulfuric acid.

The nitric acid is usually used in an amount of from 2 to 20 mole equivalents per 1 mole of compound (II), preferably from 2 to 10 mole equivalents per 1 mole of compound (II), more preferably from 2 to 8 mole equivalents per 1 mole of compound (II), most preferably from 2 to 4 mole equivalents per 1 mole of compound (II), particularly preferably from 2.1 to 2.5 mole equivalents per 1 mole of compound (II).

If the step (i) is carried out batchwise, the nitric acid is preferably used in an amount of from 2 to 8 mole equivalents per 1 mole of compound (II), preferably from 2 to 6 mole equivalents per 1 mole of compound (II), more preferably from 2 to 3.5 mole equivalents per 1 mole of compound (II), most preferably from 2 to 3 mole equivalents per 1 mole of compound (II), particularly preferably from 2.1 to 2.5 mole equivalents per 1 mole of compound (II).

If the step (i) is carried out continuously, the nitric acid is preferably used in an amount of from 2 to 20 mole equivalents per 1 mole of compound (II), preferably from 2 to 16 mole equivalents per 1 mole of compound (II), more preferably from 2 to 12 mole equivalents per 1 mole of compound (II), most preferably from 2 to 10 mole equivalents per 1 mole of compound (II), particularly preferably from 2 to 8 mole equivalents per 1 mole of compound (II).

The reaction is carried out in the presence of the sulfuric acid or oleum.

According to one embodiment, the reaction is carried out in the presence of oleum.

According to another embodiment, the reaction is carried out in the presence of the sulfuric acid.

The sulfuric acid suitable for the present invention preferably has a concentration of at least 50 mol %. Usually it has a concentration of from 50 to 100 mol %, preferably from 70 to 100 mol %, more preferably from 80 to 100 mol %, most preferably from 90 to 100 mol %, particularly preferably from 95 to 100 mol %.

The sulfuric acid is usually used in an amount of from 2 to 40 mole equivalents per 1 mole of compound (II), preferably from 3 to 30 mole equivalents per 1 mole of compound (II), more preferably from 5 to 20 mole equivalents per 1 mole of compound (II), most preferably from 5 to 10 mole equivalents per 1 mole of compound (II), particularly preferably from 5 to 7 mole equivalents per 1 mole of compound (II).

The molar ratio of the nitric acid to the sulfuric acid is usually from 1:1 to 1:20, preferably from 1:1 to 1:15, more preferably from 1:1 to 1:10, most preferably from 1:1 to 1:8, particularly preferably from 1:1 to 1:4. According to a specific embodiment, the ratio is from 1:1 to 1:2. According to a further specific embodiment, the ratio is 1:1.

The nitration according to the present invention is can be carried out at a room temperature, e.g. at 20 to 25° C. It is, however, can be carried out at elevated or reduced temperatures, usually at −30 to 80° C., preferably at −15 to 60° C., more preferably at 0 to 50° C., most preferably at 5 to 45° C., particularly preferably from 10 to 40° C.

The reaction can be carried out with or without a solvent.

According to one embodiment, the reaction is carried out without a solvent.

According to another embodiment, the reaction is carried out in a solvent. Suitable solvents are selected from halogenated aliphatic solvents, such as dichloromethane (CH$_2$Cl$_2$), chloroform (CHCl$_3$), tetrachloroethane (CCl$_4$), 1,2-dichloroethane or any mixture of the abovementioned solvents. Preferably the solvent is selected from dichloromethane, chloroform, tetrachloroethane, 1,2-dichloroethane or any mixture thereof. Alternatively, the excess of H$_2$SO$_4$ can be used as a solvent.

According to one specific embodiment, the solvent is dichloromethane.

According to another specific embodiment, the solvent is chloroform.

According to another specific embodiment, the solvent is tetrachloroethane.

According to another specific embodiment, the solvent is 1,2-dichloroethane.

According to another specific embodiment, the excess of H$_2$SO$_4$ is used as a solvent.

According to one specific embodiment, in the step (i)
a) the compound (II) is first reacted with at least 1 mole equivalent of the nitric acid per 1 mole of the compound (II) to obtain the intermediate compound (A)

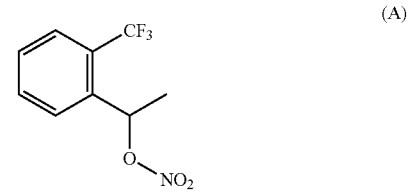

b) the water is removed from the reaction mixture and
c) the compound (A) is further reacted with 1 to 2.5 mole equivalents of the nitric acid per 1 mole of the compound (A) to obtain the compound (I).

The amount of the nitric acid used in step (i) a) is preferably from 1 to 15 mole equivalents per 1 mole of compound (II), more preferably from 1 to 10 mole equivalents per 1 mole of compound (II), most preferably from 1 to 5 mole equivalents per 1 mole of compound (II), particularly preferably from 1 to 2.5 mole equivalents per 1 mole of compound (II), specifically from 1 to 1.5 mole equivalents per 1 mole of compound (II).

In the step (i) b) the water can be removed as known to the skilled person. For example, it can be done by extracting the intermediate compound (A) with a water immiscible organic solvent, like halogenated aliphatic solvents as described above. If the reaction is carried out in a such halogenated aliphatic solvent, the organic phase can be separated from the aqueous phase as known to the skilled person. Alternatively, the stoichiometric amount of oleum can be added to the reaction mixture.

Water to be removed in the step (i) b) includes the water formed during the reaction in the step (i) a) and, in case aqueous solutions of nitric and/or sulfuric acids were employed in the step (i) a), also the water from that aqueous solutions.

According to one specific embodiment, after the step (i) a) is finished, in step (i) b) the excess of nitric acid and sulfuric acid or oleum are removed from the reaction mixture together with the water.

The order of adding the reagents to the reaction mixture is variable.

According to one embodiment, the nitric acid is pre-mixed with the sulfuric acid or oleum and this mixture is added to compound (II). The pre-mixed acids can be added to the reaction mixture in one portion or gradually. According to one embodiment they are added to the reaction mixture in one portion. According to another embodiment they are added to the reaction mixture gradually. Gradual addition is preferred.

According to another embodiment, compound (II) is added to the pre-mixed acid comprising nitric acid and sulfuric acid or oleum. The compound (II) can be added to the reaction mixture in one portion or gradually. According to one embodiment it is added to the reaction mixture in one portion. According to another embodiment it is added to the reaction mixture gradually. Gradual addition is preferred.

After step (i), a work-up of the reaction mixture can be carried out by procedures known in a general manner to the person skilled in the art. For example, the reaction mixture is diluted with water or ice and the aqueous phase is extracted with a suitable solvent, e.g. toluene or oxylene. If the reaction is run in the presence of halogenated organic solvents, the organic phase containing the product can be separated directly from the nitration acid. The organic phases can be washed with water to remove residual acid, if necessary. The raw product obtained after evaporation of the solvent(s) can directly be used in a further step, if desired. However, the raw product can also be further worked up and/or purified as generally known to the skilled person.

The process can further comprise a further step (ii) according to which the excess of the nitric acid and sulfuric acid or oleum is separated from the reaction mass after step (i) is finished and returned back to the nitration step (i). If necessary, prior to returning the separated acids to step (i) the concentration of said acids can be adjusted to reach the initial concentration.

According to one specific embodiment, the excess of the nitric acid and sulfuric acid or oleum is returned to step (i) a).

The separation can be carried out by procedures known in a general manner to the person skilled in the art. The separates are then treated with oleum or sulfur trioxide in order to remove the water formed during the reaction and achieve the initial concentration of the sulfuric acid. The recycled concentrated sulfuric acid is reused in the production process.

The invention is illustrated by the following examples without being limited thereto or thereby.

Experimental Part

HPLC-method: Agilent 1200; column: Hailo C-18 150× 4,6 mm; mobile phase A: acetonitrile, mobile phase B: $H_2O$ +0.5% 0.5 mol/L $H_2SO_4$; flow 1.0 mL/min; gradient: 0 min 80% B-15 min 22% B-18 min 0% B-20min 80% B; temperature 30° C., wavelength 230 nm Product is at 13.6 min

EXAMPLE 1

12.5 mL 100% nitric acid (0.30 mol) was treated with 25 mL 96% sulfuric acid (0.47 mol) with cooling. 2.9 g molten α-methyl-2-(trifluoromethyl)-benzyl alcohol (15 mmol) was added to the mixture within 10 min while keeping the temperature at 0-5° C. After 15 min a solid precipitated from the mixture. The entire mixture was poured into 250 ml cold water and the product extracted with 50 mL $CH_2Cl_2$. The organic phase was washed with aqueous sodium bicarbonate and water. The $CH_2Cl_2$ was removed by rotary evaporation keeping the temperature below 25° C. The product was obtained as an oil which solidified upon standing in a few minutes. Yield 4.1 g, (14.6 mmol), 97% by qualitative HPLC, essentially pure by NMR.

$^1$H-NMR: (500 MHz, $CDCl_3$): 8.58 (d, 1H, J=2.0 Hz), 8.48 (dd, 1H, J=8.6, 2.0 Hz), 7.89 (d, 1H, J=8.6 Hz), 6.32 (q, 1H, J=6.6 Hz), 1.65 (d, 3H, J=6.6 Hz) ppm. $^{13}$C-NMR: (125 MHz, $CDCl_3$): 20.8, 76.3 (q, J=2.5 Hz), 121.9 (q, J=6.0 Hz), 122.7 (q, J=275 Hz), 127.6, 127.7, 128.7 (q, J=33.1 Hz), 145.9, 147.5

EXAMPLE 2

10 g 65% nitric acid (0.10 mol) was treated with 31 g 98% sulfuric acid (0.31 mol) with cooling. 5.0 g molten α-methyl-2-(trifluoromethyl)-benzyl alcohol (26 mmol) was added to the mixture while the temperature was allowed to reach 50-55° C. The mixture cooled down to 23° C. and was post-stirred for 1 h before it was poured into 65 g of cold water. The temperature reached 55° C. The precipitated product was filtered and washed with 15 g water, followed by 2×15 g 5% aqueous sodium bicarbonate solution and 2×15 g water. The product was dried at 60° C./80 mbar. Yield 6.5 g, (24.3 mmol), 97% by qualitative HPLC, essentially pure by NMR.

EXAMPLE 3

28.5 g 99% nitric acid (0.45 mmol) was added slowly to 105 g 98% sulfuric acid (1.05 mol) with cooling. 61.5 g 1,2-dichloroethane was added. 28.5 g α-methyl-2-(trifluoromethyl)-benzyl alcohol (0.15 mol), dissolved in 28.5 g 1,2-dichloroethane, was added within 48 min while keeping the temperature at 19-23° C. The biphasic mixture was post-stirred for 5 h. The phases were separated. The organic phase contained 98% yield of the desired product by quantitative HPLC.

EXAMPLE 4

18.4 g 98% sulfuric acid (184 mmol) is added to nitric acid 11.7 g 99% nitric acid (184 mmol) at 0° C. to form nitrating acid. α-methyl-2-(trifluoromethyl)-benzyl alcohol (5 g, 26.3 mmol) is dissolved in 1,2-dichloromethane (15 mL). Said solution and the nitrating acid are dosed to a continuous reactor maintained at 40° C. with a rate of an approximately 2 mL/min per solution. The reactor is rinsed with 1,2-dichloromethane (12 mL) after the dosing is finished. The combined phases are collected, the organic phase is separated and characterized via HPLC. The content of the desired product is 20.9% w/w (yield 91%).

EXAMPLE 5

α-methyl-2-(trifluoromethyl)-benzyl alcohol (28.5 g, 150 mmol) was dissolved in 1,2-dichloroethane (90 g) and the solution cooled to 0° C. A mixture of 11.2 g nitric acid (99%, 0.18 mol, 1.2 eq) and 17.7 g sulfuric acid (98%, 0.18 mol, 1.2 eq) was added within 27 min under intensive stirring, keeping the temperature at 0-5° C. Stirring was continued for 90 min at 5° C. and the phases were separated. The upper organic phase containing α-methyl-2-(trifluoromethyl)-benzyl nitrate was left in the reactor. A mixture of 14.0 g nitric acid (99%, 0.22 mol, 1.5 eq) and 29.4 g sulfuric acid (98%, 0.30 mol, 2.0 eq) was added within 30 min under intensive stirring, keeping the temperature at 2-9° C. The mixture was post-stirred over night at 15-20° C. The phases were separated and the organic phase (109.9 g) was analyzed. The content of the desired product was 34.2% w/w (134 mmol, yield 89%).

EXAMPLE 6

A mixture of 160 g 96% sulfuric acid (1.57 mol) and 101 g 98% nitric acid (1.57 mol) was prepared. Of this mixture, 0.55 g/min (0.30 mL/min, 3.2 mmol/mol, 5.8 eq) was continuously pumped into a 5 ml vessel with overflow. In parallel, a 25 wt % solution of α-methyl-2-(trifluoromethyl)-benzyl alcohol in 1,2-dichloroethane (0.32 mL/min, 0.42 g/min, 0.55 mmol/min) was pumped into the vessel with intense stirring. The temperature was kept at 20° C. by external cooling. After reaching a steady state, the product flow was collected. The phases were separated, and the organic phase was washed with water. Quantitative HPLC analysis of the dichloroethane solution showed a product concentration of 31.0 wt % corresponding to 94% chemical yield.

EXAMPLE 7

4.0 g nitric acid (99 wt %, 64 mmol, 0.15 eq) and 141.4 g sulfuric acid (98 wt %, 1.41 mol, 3.0 eq) are mixed with cooling. 152 g 1,2-dichloroethane is added. The mixture is cooled to 5° C. A solution of 90.0 g α-methyl-2-(trifluoromethyl)-benzyl alcohol (0.47 mol) in 129 g 1,2-dichloroethane is added within 118 min. In parallel, 86 g nitric acid (99 wt %, 1.35 mol, 2.85 eq) is added within 97 min. During the first half of the additions, the temperature is kept at maximum 5° C. and for the rest of the dosage at maximum 15° C. The biphasic mixture is post-stirred for 5 h at 20° C. The phases are separated. Quantitative HPLC analysis of the dichloroethane solution (422 g) showed a product concentration of 28.8 wt % corresponding to 92% chemical yield.

The isolated dry product (compound (I)) is shock-sensitive.

The invention claimed is:

1. A process for preparing a compound of formula (I)

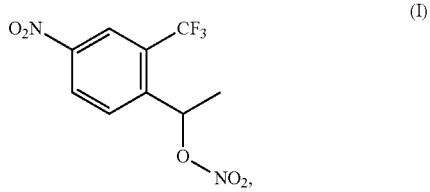 [SMILES: CC(O[N+](=O)[O-])c1ccc([N+](=O)[O-])cc1C(F)(F)F]

comprising:
(ii) reacting a compound of formula (II)

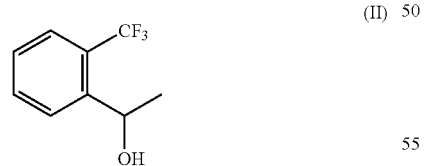

with nitric acid in the presence of sulfuric acid or oleum, wherein the nitric acid is used in an amount of 2 to 20 mole equivalents per 1 mole of the compound (II).

2. The process of claim 1, wherein the nitric acid is used in an amount of 2 to 10 mole equivalents per 1 mole of the compound (II).

3. The process of claim 1, wherein the nitric acid has a concentration of from 95 to 100 mol % or is a fuming nitric acid.

4. The process of claim 1-to 4, wherein the reaction is carried out in the presence of the sulfuric acid.

5. The process of claim 1, wherein the sulfuric acid has a concentration of from 95 to 100 mol %.

6. The process of claim 1, wherein the reaction is carried out in the presence of oleum.

7. The process of claim 1, wherein a molar ratio of the nitric acid to the sulfuric acid or oleum is from 1:1 to 1:20.

8. The process of claim 1, wherein the molar ratio of the nitric acid to the sulfuric acid or oleum is from 1:2 to 1:6.

9. The process of claim 1, wherein the reaction is carried out in a chlorinated aliphatic solvent.

10. The process of claim 1, wherein in a step (i)
a) the compound (II) is first reacted with at least 1 mole equivalents of the nitric acid per 1 mole of the compound (II) to obtain an intermediate compound (A)

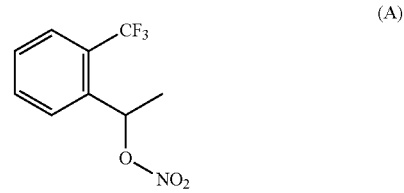 [SMILES: CC(O[N+](=O)[O-])c1ccccc1C(F)(F)F]

b) water, optionally together with the excess of the nitric acid and sulfuric acid or oleum, is removed from the reaction mixture and
c) the compound (A) is further reacted with 1 to 2.5 mole equivalents of the nitric acid per 1 mole of the compound (A) to obtain the compound (I).

11. The process of claim 10, wherein in the step (i) a) 1 to 1.5 mole equivalents of the nitric acid per 1 mole of the compound (II) are used.

12. The process of claim 1, carried out in a continuous mode of operation.

13. The process of claim 10, further comprising
(iii) separating excess of the nitric acid and sulfuric acid or oleum from the reaction mass, optionally adjusting the concentration to reach an initial concentration, and thereafter returning it to the nitration step i).

14. The process of claim 13, wherein excess of the nitric acid and sulfuric acid or oleum is returned to step i) a).

15. A compound of formula (I) or formula (A)

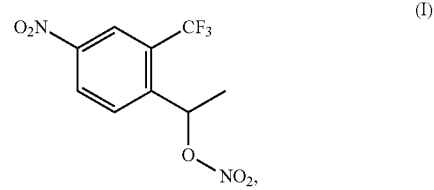 [SMILES: CC(O[N+](=O)[O-])c1ccc([N+](=O)[O-])cc1C(F)(F)F]

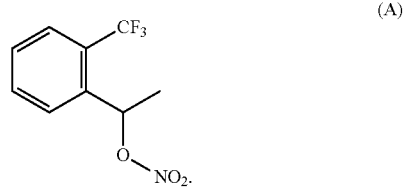 [SMILES: CC(O[N+](=O)[O-])c1ccccc1C(F)(F)F]

* * * * *